(12) United States Patent
Imai (10) Patent No.: US 10,660,680 B2
(45) Date of Patent: May 26, 2020

(54) BONE TREATING DEVICE, BONE TREATING SCREW AND BONE TREATING PLATE

(71) Applicant: Meira Corporation, Nagoya-shi, Aichi (JP)

(72) Inventor: Takahiro Imai, Seki (JP)

(73) Assignee: MEIRA CORPORATION, Nagoya-Shi, Aichi (JP)

(*) Notice: Subject to any disclaimer, the term of this patent is extended or adjusted under 35 U.S.C. 154(b) by 120 days.

(21) Appl. No.: 15/941,356

(22) Filed: Mar. 30, 2018

(65) Prior Publication Data

US 2019/0231402 A1 Aug. 1, 2019

(30) Foreign Application Priority Data

Jan. 26, 2018 (JP) ................................. 2018-011643

(51) Int. Cl.
*A61B 17/80* (2006.01)
*A61B 17/86* (2006.01)

(52) U.S. Cl.
CPC ........ *A61B 17/8057* (2013.01); *A61B 17/863* (2013.01)

(58) Field of Classification Search
CPC . A61B 17/80; A61B 17/8052; A61B 17/8057; A61B 17/86; A61B 17/861; A61B 17/8615; A61B 17/8625; A61B 17/863; A61B 17/8635; F16B 35/047
USPC ........................................................ 411/386
See application file for complete search history.

(56) References Cited

U.S. PATENT DOCUMENTS

| | | | |
|---|---|---|---|
| 5,730,566 A * | 3/1998 | Goodwin ................ | F16B 33/02 411/386 |
| 5,791,849 A * | 8/1998 | Goodwin .............. | F16B 35/047 411/386 |
| 5,836,731 A * | 11/1998 | Goodwin ................ | F16B 33/02 411/386 |
| 6,730,091 B1* | 5/2004 | Pfefferle ............ | A61B 17/8057 606/291 |
| 8,292,898 B2 | 10/2012 | Castaneda et al. | |
| 8,518,088 B2 | 8/2013 | Castaneda et al. | |
| 8,940,029 B2* | 1/2015 | Leung ................ | A61B 17/8605 606/287 |

(Continued)

FOREIGN PATENT DOCUMENTS

WO 2010030847 A1 3/2010

*Primary Examiner* — Eric S Gibson
(74) *Attorney, Agent, or Firm* — Buchanan Ingersoll & Rooney PC (57) ABSTRACT

A bone treating device has a bone plate and a bone screw. The bone plate has an opening which penetrates therethrough and has a female screw part having a plurality of thread grooves formed on an inner surface of the opening. The bone screw has a shaft part capable of penetrating the opening of the bone plate and a head part provided at a proximal end of the shaft part. The head part has on an outer surface thereof a male screw part having a plurality of screw threads threadedly engageable with the thread grooves of the female screw part formed on the inner surface of the opening. The bone screw has a threaded engagement start guiding portion formed by extending screw threads whose number is fewer by at least one than the number of screw threads formed in the male screw part to a threaded engagement start side.

17 Claims, 10 Drawing Sheets

(56) References Cited

U.S. PATENT DOCUMENTS

| | | | |
|---|---|---|---|
| 2005/0065521 A1 | 3/2005 | Steger et al. | |
| 2009/0312803 A1* | 12/2009 | Austin | A61B 17/8014 606/305 |
| 2010/0057138 A1* | 3/2010 | Murner | A61B 17/1728 606/308 |
| 2010/0217332 A1* | 8/2010 | Daniels | A61B 17/8061 606/305 |
| 2013/0150902 A1* | 6/2013 | Leite | A61B 17/8057 606/291 |
| 2013/0261675 A1* | 10/2013 | Fritzinger | A61B 17/8057 606/291 |
| 2014/0005728 A1* | 1/2014 | Koay | A61B 17/8057 606/281 |
| 2014/0018862 A1* | 1/2014 | Koay | A61B 17/8057 606/281 |
| 2014/0058455 A1* | 2/2014 | Appenzeller | A61B 17/8057 606/281 |
| 2015/0051651 A1* | 2/2015 | Terrill | A61B 17/8057 606/289 |
| 2015/0223853 A1* | 8/2015 | Appenzeller | A61B 17/8057 606/281 |
| 2015/0316089 A1* | 11/2015 | Pritchard | F16B 35/047 411/366.3 |
| 2019/0231402 A1* | 8/2019 | Imai | A61B 17/8057 |

\* cited by examiner

BONE TREATING DEVICE, BONE TREATING SCREW AND BONE TREATING PLATE

FIELD OF THE INVENTION

The present invention relates to a fractured bone treating device (hereinafter referred to as bone treating device), a fractured bone treating screw (hereinafter referred to as bone screw), and a fractured bone treating plate (hereinafter referred to as bone plate).

DESCRIPTION OF THE RELATED ART

As a means for treating a fractured portion of bone, a bone plate, a bone screw for fixing the bone plate to bone, and a bone treating device having the bone plate and the bone screw are used. Bone plates having an opening for fixing the bone screw thereto are known. As disclosed in WO2010030847 (patent document 1, U.S. Pat. Nos. 8,292,898, 8,518,088) and in US2005/065521(A1) (patent document 2), bone plates having the female screw part formed on the inner surface of the opening to which a screw is fixed is known.

The bone screw (see FIG. 29 of patent document 1 and FIG. 5 of patent document 2) having the male screw part threadedly engageable with the female screw part at its head part is used for such bone plates. There is a lot of uses of the bone plate not having the female screw part and the bone screw not having the male screw part. But the bone plate having the female screw part and the bone screw having the male screw part can be fixed to bone more effectively than the bone plate not having the female screw and the bone screw not having the male screw. The head part 48 of the bone screw of the patent document 2 has two screw threads.

Because the above-described bone screw has two screw threads, in threadedly engaging the male screw part of the bone screw with the female screw part of the bone plate, all of the screw threads of the male screw part of the bone screw are required to threadedly engage the thread grooves of the female screw part of the bone plate all together. To this end, when the male screw part starts to threadedly engage the female screw part, the axis of the female screw part and that of the male screw part are required to align with each other more accurately than a threaded engagement between a single screw thread and a single thread groove. In the conventional bone treating device, when female and male screw parts are slightly dislocated in the angle and position of the axes thereof at the start of the threaded engagement between both screw parts, it often occurs that both screw parts do not engage each other and thus an operation of threadedly engaging both screw parts each other is performed again. Conventional bone treating devices have a problem in that the engaging operation cannot be performed smoothly and securely.

The present invention has been developed to solve the above-described problems of the conventional art. Therefore, it is an object of the present invention to provide a bone screw, a bone plate, and a bone treating device having the bone screw and the bone plate. More specifically, the present invention is intended to provide a bone treating device in which a male screw part of a bone screw consisting of a multiple threaded screw is smoothly and securely engageable with a female screw part of a bone plate consisting of a multiple threaded screw.

SUMMARY OF THE INVENTION

The bone treating device which achieves the above-described object of the present invention has the following construction:

The bone treating device has a bone plate and a bone screw.

The bone plate has an opening which penetrates therethrough and has a female screw part having a plurality of thread grooves formed on an inner surface of the opening. The bone screw has a shaft part capable of penetrating the opening of the bone plate and a head part, provided at a proximal end of the shaft part, The head part of the bone screw has a male screw part having a plurality of screw threads threadedly engageable with the thread grooves of the female screw part of the bone plate. The bone screw or the bone plate has a threaded engagement start guiding portion formed by extending screw threads or thread grooves whose number is fewer by at least one than the number of screw threads or thread grooves formed in the male screw part or in the female screw part to a threaded engagement start side.

The bone screw which achieves the above-described object of the present invention has the following construction:

The bone screw can be fixed to a bone plate has an opening which has a female screw part having a plurality of thread grooves formed on an inner surface of the opening. The bone screw has a shaft part capable of penetrating the opening of the bone plate and a head part, provided at a proximal end of the shaft part, which has on an outer surface thereof a male screw part having a plurality of screw threads threadedly engageable with the thread grooves of the female screw part formed on the inner surface of the opening. The bone screw has a threaded engagement start guiding portion formed by extending screw threads whose number is fewer by at least one than a number of the screw threads formed in the male screw part to a threaded engagement start side.

The bone plate which achieves the above-described object of the present invention has the following construction:

The bone plate has an opening for fixing the bone screw thereto. The opening has a female screw part having a plurality of thread grooves formed on an inner surface thereof and a threaded engagement start guiding portion formed by extending thread grooves whose number is fewer by at least one than the number of the thread grooves formed in the female screw part to a threaded engagement start side.

DESCRIPTION OF THE PREFERRED EMBODIMENTS

The bone treating instrument, bone screw, and bone plate of the present invention are described below with reference to the drawings showing the embodiments of the present invention.

A bone treating device 1 of the present invention has a bone plate 5 and a bone screw 2. The bone plate 5 has an opening 62 which penetrates therethrough and which has a female screw part 63 having a plurality of thread grooves formed on an inner surface of the opening 62. The bone screw 2 has a shaft part 21 capable of penetrating the opening 62 of the bone plate 5 and a head part 30 provided at a proximal end of the shaft part 21. The head part 30 has on an outer surface thereof a male screw part having a plurality of screw threads threadedly engageable with the thread grooves of the female screw part 63 formed on the inner surface of the opening 62. The bone screw 2 or the bone plate 5 has a threaded engagement start guiding portion 36 formed by extending screw threads or thread grooves whose number is fewer by at least one than the number of screw threads or the number of thread grooves formed at the male screw part or in the female screw part to a threaded engagement start side.

Figure 1:
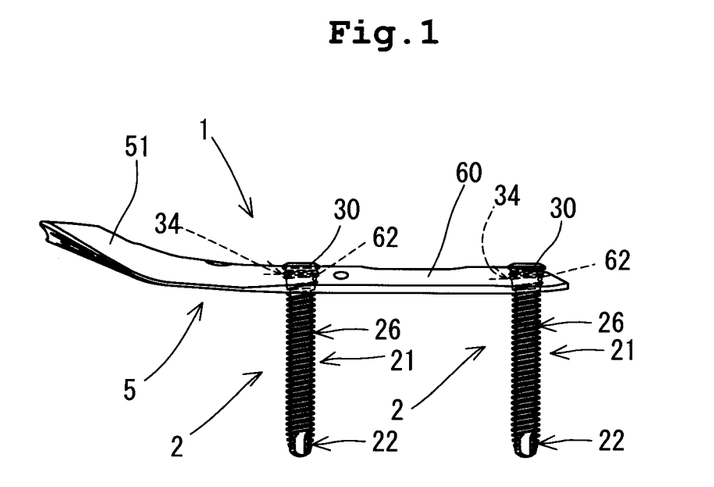
FIG. 1 is a front view of a bone treating device of the present invention.

The bone treating device 1 of the embodiment shown in FIG. 1 is so constructed as to catch fractured parts of bone and fix them to the bone plate 5 and is thus applicable to treatment of various types of fractures. The bone treating device 1 has the bone screw 2 and the bone plate 5. As shown in FIG. 3 and FIGS. 6 through 11, the head part 30 of the bone screw 2 has the male screw part (male screw part for fixing the bone screw 2 to the bone plate 5). The male screw part has a threadedly engaging portion having a plurality of screw threads (more specifically, three screw threads) and the threaded engagement start guiding portion 36 formed by extending a first screw thread 35 consisting of one screw thread (fewer than the number of the screw threads of the male screw part by two) of the three screw threads of the threadedly engaging portion to the threaded engagement start side, namely, toward the distal side of the bone screw 2. In the bone treating device 1 of this embodiment, the threaded engagement start guiding portion 36 is formed by extending only one screw thread or only one thread groove of the male screw part or the female screw part to the threaded engagement start side.

Figure 2:
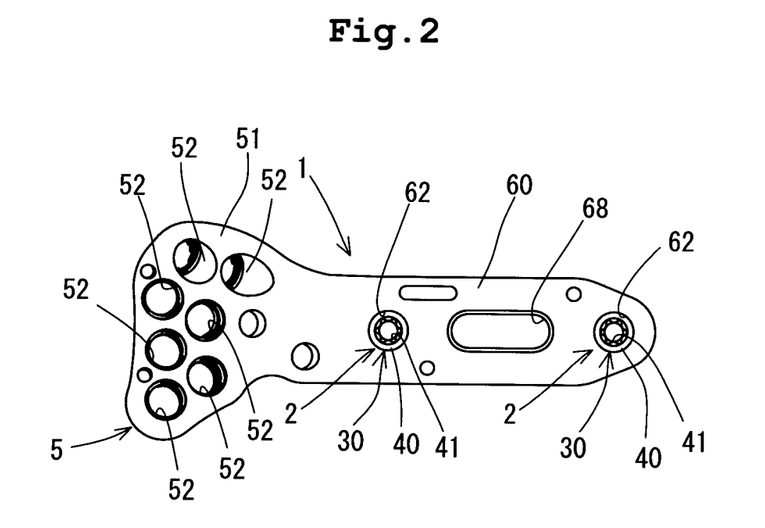
FIG. 2 is a plan view of the bone treating device shown in FIG. 1.
Figure 3:
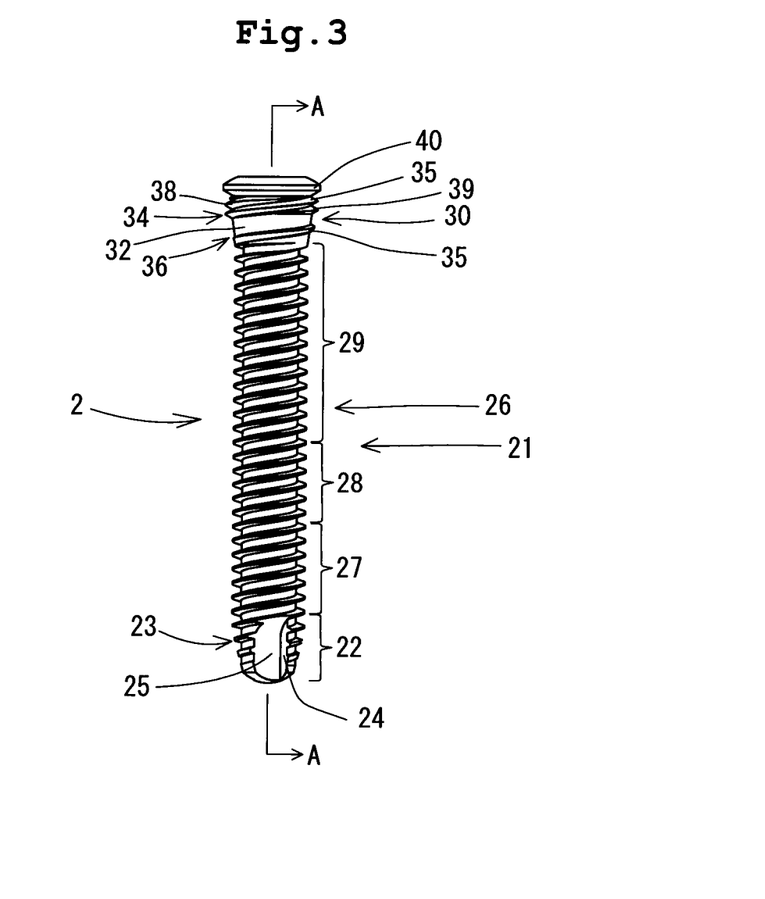
FIG. 3 is an enlarged front view of a bone screw of the present invention for use in the bone treating device shown in FIG. 1.

The bone treating device 1 shown in FIGS. 1 and 2 has the bone plate 5 and the bone screw 2 having the head part 30 threadedly engageable with the two openings 62 formed in penetration through a body 60 of the bone plate 5 (hereinafter referred to as plate body 60).

As shown in FIGS. 3 through 10, the bone screw 2 has the shaft part 21 and the head part 30. The shaft part 21 has a self-tapping portion 22 disposed at a distal end side thereof and a screw portion 26, to be inserted into bone (hereinafter referred to as merely screw portion 26), which is disposed at a side proximal from the self-tapping portion 22. The screw portion 26 has a first bone screw portion 27, a back tapered portion 28, and a second bone screw portion 29 arranged sequentially in this order from its distal end to its proximal end.

As shown in FIG. 3 and FIGS. 5 through 10, the self-tapping portion 22 has a male screw 23 and three blades 24 formed by cutting off the self-tapping portion 22 along the axis of the self-tapping portion 22 in such a way that the blades 24 are equiangularly spaced from one another with respect to the axis of the screw 2. A concave portion 25 for accommodating powdered bone therein is formed at a front side of each blade 24 in a rotational direction of the bone screw 2 in screwing the screw portion 26 into the bone. The self-tapping portion 22 tapers off at a predetermined angle (specifically 10 to 20 degrees) to its distal end in the outer diameter including the screw thread of the male screw 23 and the diameter of the root of the male screw 23 so as to allow the self-tapping portion 22 to easily screw into the bone. In this embodiment, the blades 24 of the self-tapping portion 22 are formed up to a position spaced at about 2.5 mm from the distal end of the bone screw 2.

The first bone screw portion 27 is provided continuously with a proximal end of the self-tapping portion 22. The outer diameter of the first bone screw portion 27 of this embodiment including the length of its screw thread is set to favorably 2.0 to 7.5 mm and more favorably 2.5 to 4.0 mm, although the outer diameter of the first bone screw portion 27 is different according to a portion of the bone to be treated. The outer diameter of the root of the first bone screw portion 27 is set to favorably 5/10 to 8/10 and more favorably 65/100 to 75/100 of the outer diameter of the screw thread. The length of the screw thread of the first bone screw portion 27 is set to favorably 0.4 to 1.2 mm and more favorably 0.6 to 1.0 mm. In this embodiment, it is preferable to form the first bone screw portion 27 at a position spaced at 3.0 mm from the distal end of the bone screw 2 to a position spaced at 10.0 mm from the distal end thereof.

The back tapered portion 28 having a male screw similar to that of the first bone screw portion 27 is provided continuously with a proximal end of the first bone screw portion 27. The back tapered portion 28 is so formed that its outer diameter becomes gradually smaller (more specifically, gradually and slightly smaller) from the proximal end of the first bone screw portion 27 to the distal end of the second bone screw portion 29 to be described later. This configuration of the back tapered portion 28 is capable of slightly decreasing the resistance of the inner circumferential surface of the hole of the bone formed by cut-off operation performed by the self-tapping portion 22 to the back tapered portion 28 after the first bone screw portion 27 is screwed into the bone. Thus, in further screwing the bone screw 2 into the bone, the bone screw 2 can be smoothly screwed into the bone. In this embodiment, it is preferable to set the length of the back tapered portion 28 to 1.5 to 2.5 mm.

The second bone screw portion 29 is provided in a range from a proximal end of the back tapered portion 28 to a distal end of the head part 30 with the distal end of the second bone screw portion 29 being continuous with the proximal end of the back tapered portion 28. The outer diameter of the second bone screw portion 29 of this embodiment including the length of the screw thread thereof, the outer diameter of the root thereof, and the length of the screw thread thereof are set equally to those of the proximal region of the back tapered portion 28.

The self-tapping portion 22, the first bone screw portion 27, the back tapered portion 28, and the second bone screw portion 29 have an equal pitch in the male screws thereof. The pitches of the male screws thereof are set to favorably 0.4 to 2.0 mm and more favorably 0.5 to 1.5 mm.

Figure 4:
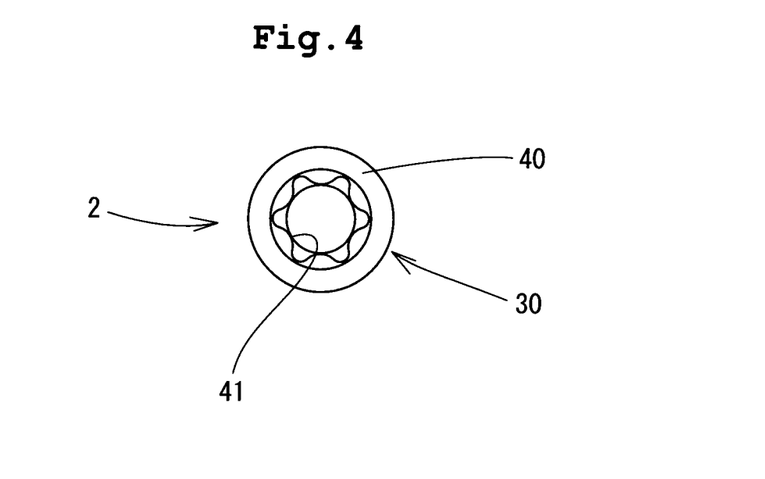
FIG. 4 is an enlarged plan view of the bone screw shown in FIG. 3.
Figure 5:
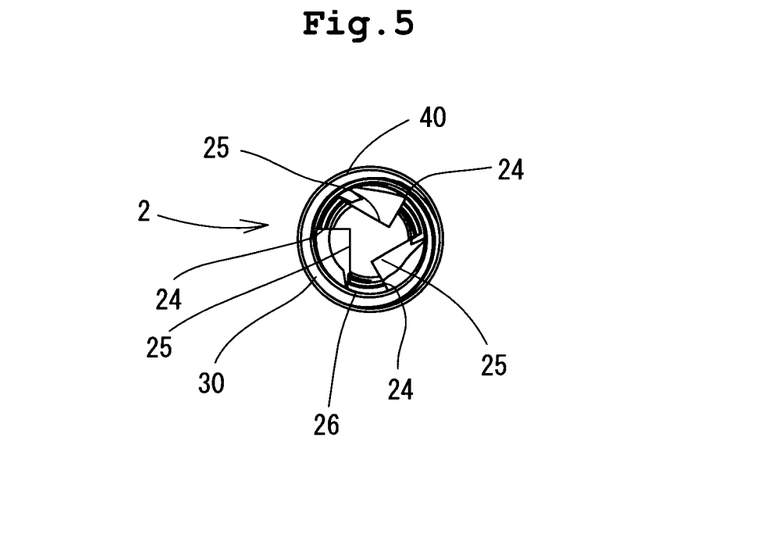
FIG. 5 is an enlarged bottom view of the bone screw shown in FIG. 3.
Figure 6:
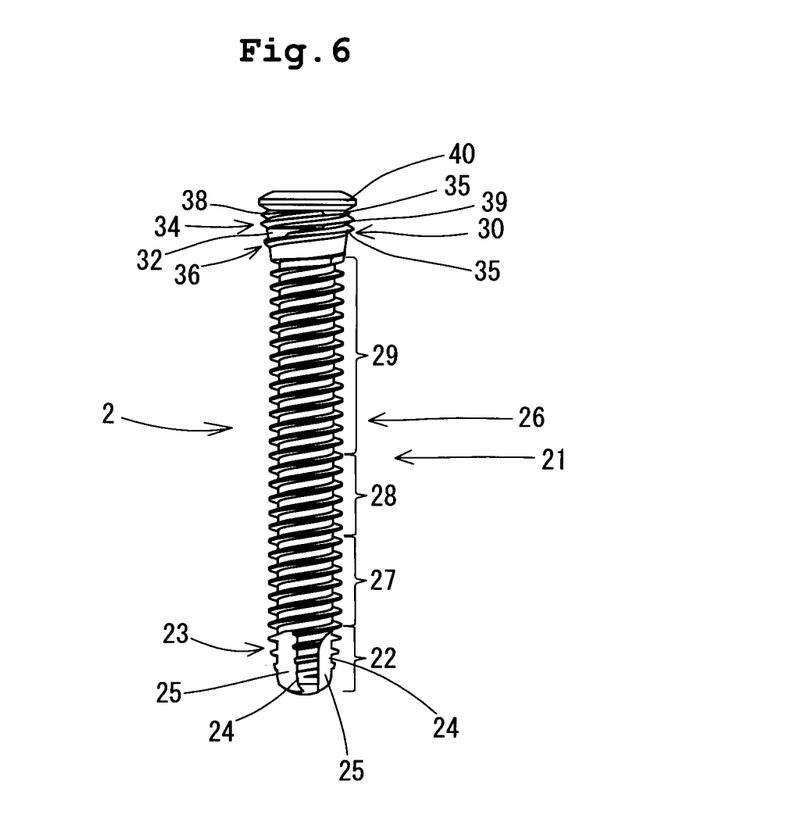
FIG. 6 is a rear view of the bone screw shown in FIG. 3.
Figure 7:
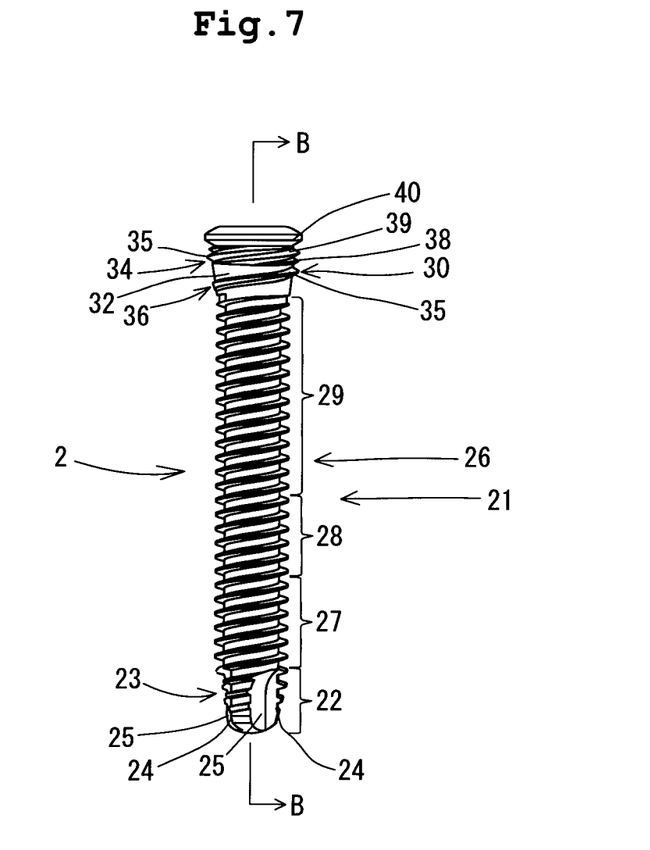
FIG. 7 is a right side view of the bone screw shown in FIG. 3.
Figure 9:
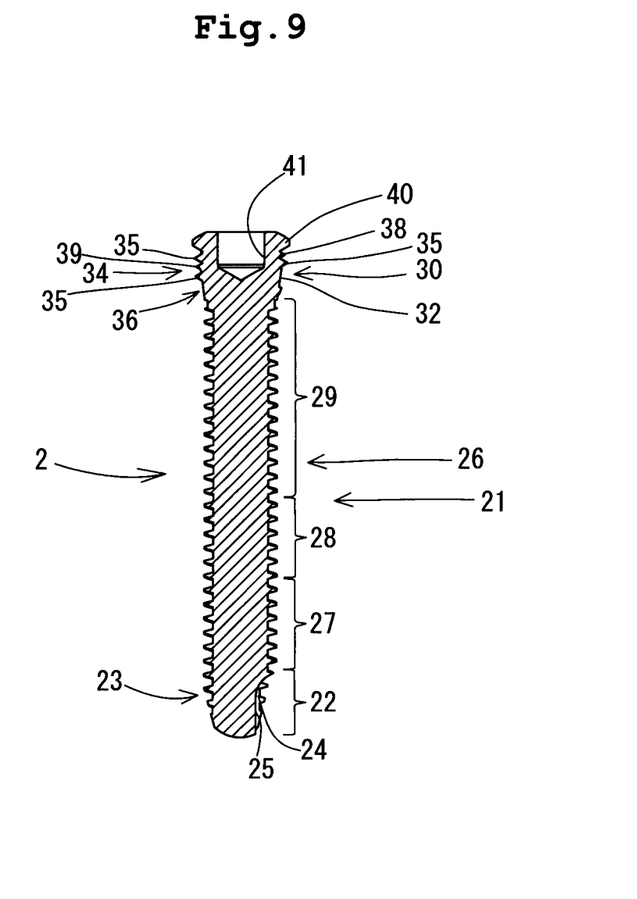
FIG. 9 is a sectional view of the bone screw shown in FIG. 3 taken along a line A-A.
Figure 10:
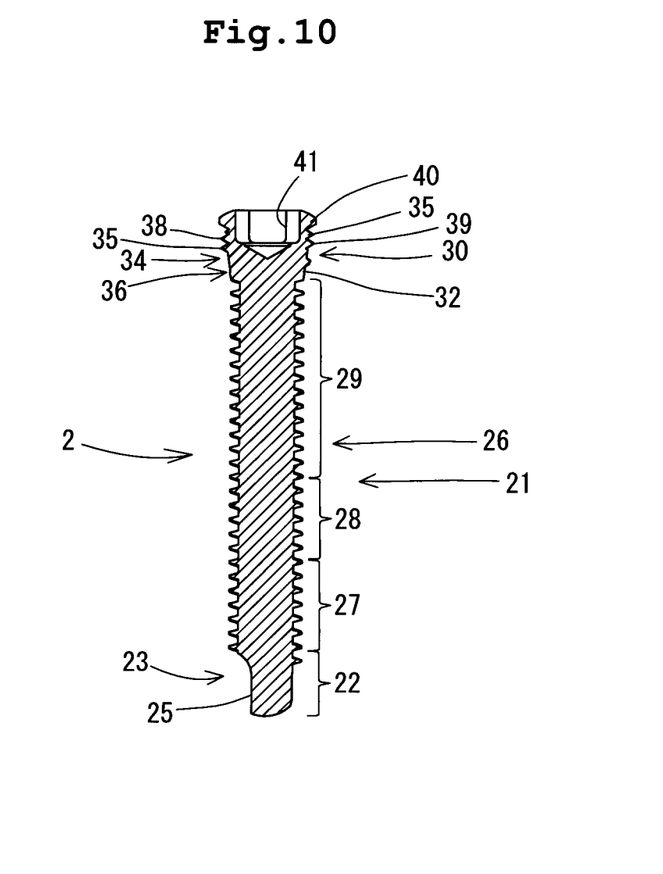
FIG. 10 is a sectional view of the bone screw shown in FIG. 7 taken along a line B-B.

The head part 30 of the bone screw 2 is described below. The head part 30 has a tapered portion 32 extended from the shaft part 21 and a flange portion 40 provided at a side proximal from the tapered portion 32 to form the proximal end of the bone screw 2. The outer diameter of the flange portion 40 is set larger than that of the tapered portion 32. As shown in FIGS. 4, 9, and 10, the head part 30 has a concave portion 41 to which a rotating jig (for example, driver) is connected. The configuration of the concave portion 41 corresponds to that of a distal end of the rotating jig.

Figure 11:
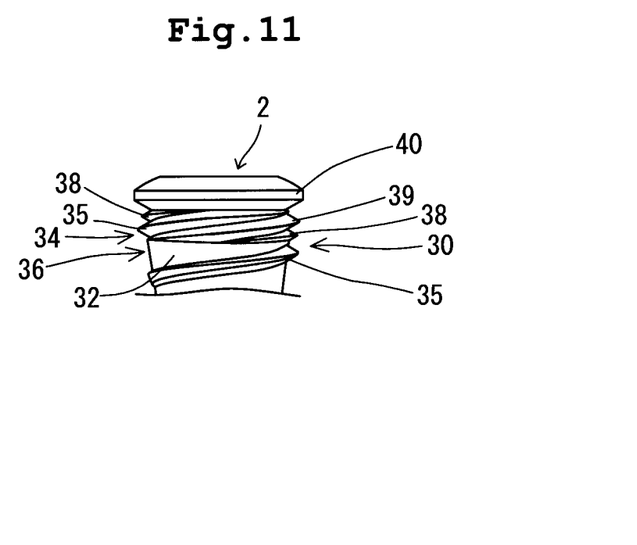
FIG. 11 is enlarged view of main parts of the bone screw shown in FIG. 3 when the bone screw is seen in a right side view.

As shown in FIG. 3 and FIG. 6 through 11, the head part 30 of the bone screw 2, namely, the tapered portion 32 of the head part 30 has a male screw part (for fixing the bone screw 2 to the bone plate 5) 34. The male screw part 34 has the threadedly engaging portion having a plurality of the screw threads (more specifically, three screw threads) and the threaded engagement start guiding portion 36 formed by extending the first screw thread 35 consisting of one of three screw threads to the threaded engagement start side, namely, toward the distal side of the bone screw 2. More specifically, as shown in FIG. 11, the tapered portion 32 is provided with the male screw part 34, consisting of a triple threaded screw, which is formed along three parallel helixes. The tapered portion 32 tapers off to its distal end at a predetermined angle (more specifically, 15 to 30 degrees and preferably 20 to 25 degrees) in the outer diameter thereof including the screw thread of the male screw part 34 and in the diameter of the root thereof. The male screw part 34 has a first screw thread 35, a second screw thread 38, and a third screw thread 39. Of the three screw threads 35, 38, and 39, only the first screw thread 35 is extended to the threaded engagement start side, namely, toward the distal side of the bone screw 2. A portion of the first screw thread 35 extended to the threaded engagement start side forms the threaded engagement start guiding portion 36.

By providing the bone screw 2 with the threaded engagement start guiding portion 36, the engagement between the screw threads of the threadedly engaging portion (having a plurality of the screw threads) of the male screw part 34 and the thread grooves of the female screw part 63 of the bone plate 5 starts when only the first screw thread 35 engages the thread grooves of the female screw part 63. Therefore, it is unnecessary for a plurality of the screw threads 35, 38, and 39 of the male screw part 34 to engage the thread grooves of the female screw part 63 all together. Thereby it is unnecessary for the axis of the head part 30 and that of the female screw part 63 to align with each other in an early stage of the threaded engagement between the thread grooves of the female screw part 63 and the threadedly engaging portion of the male screw part 34 of the first screw thread 35. Thus, the head part 30 is allowed to have a degree of freedom in its angle and position. With the progress of the engagement between the first screw thread 35 and the female screw part 63 to a certain extent, the angle and position of the head part 30 are gradually corrected and consequently the axis of the head part 30 and that of the female screw part 63 of the bone plate 5 are aligned with each other. As a result of the aligning between the axis of the male screw of the head part 30 and that of the female screw part 63 of the bone plate 5, it becomes easy for the second and third screw threads 38 and 39 not extended to the threaded engagement start side unlike the first screw thread 35 to engage the thread grooves of the female screw part 63 after the first screw thread 35 engages the thread grooves of the female screw part 63.

Figure 8:
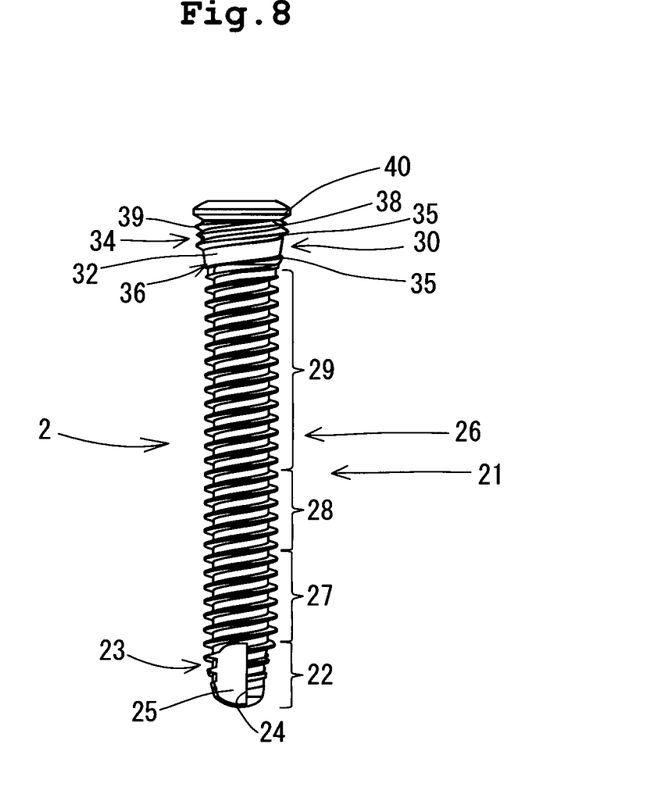
FIG. 8 is a left side view of the bone screw shown in FIG. 3.

In the bone screw 2, the first screw thread 35 forming the threaded engagement start guiding portion 36 is extended in a predetermined length about the axis of the head part 30 from an end of the threaded engagement start side of the second and third screw threads 38 and 39 in the axial direction of the head part 30 of the bone screw 2. The first screw thread 35 forming the threaded engagement start guiding portion 36 is extended at favorably not less than 180 degrees and more favorably not less than 270 degrees about the axis of the bone screw 2 from an end of the threaded engagement start side of the second and third screw threads 38 and 39. The first screw thread 35 of this embodiment is extended at about 360 degrees about the axis of the bone screw 2 from an end of the threaded engagement start side of the second and third screw threads 38 and 39. As shown in FIG. 8, the distal end of the first screw thread 35 tapers distally. Thereby the first screw thread 35 is capable of easily entering the thread grooves of the female screw part 63 of the screw plate 5.

The lead of the male screws (the screw threads of the threadedly engaging portion and the screw thread of the threaded engagement start guiding portion 36) of the male screw part 34 of the head part 30 is set substantially equally to the lead of each of the first bone screw portion 27, the back tapered portion 28, and the second bone screw portion 29. In the bone screw of this embodiment, the threadedly engaging portion of the male screw part 34 of the head part 30 has three screw threads, whereas the shaft part (consisting of the first bone screw portion 27, the back tapered portion 28, and the second bone screw portion 29) 21 has two screw threads. Although the number of the screw threads of the threadedly engaging portion of the male screw part 34 and that of the shaft part 21 are different from each other, the screw portion of the shaft part 21 does not become an obstacle in threadedly engaging the male screw part (screw threads) 34 of the head part 30 with the female screw part 63 of the bone plate 5.

Figure 12:
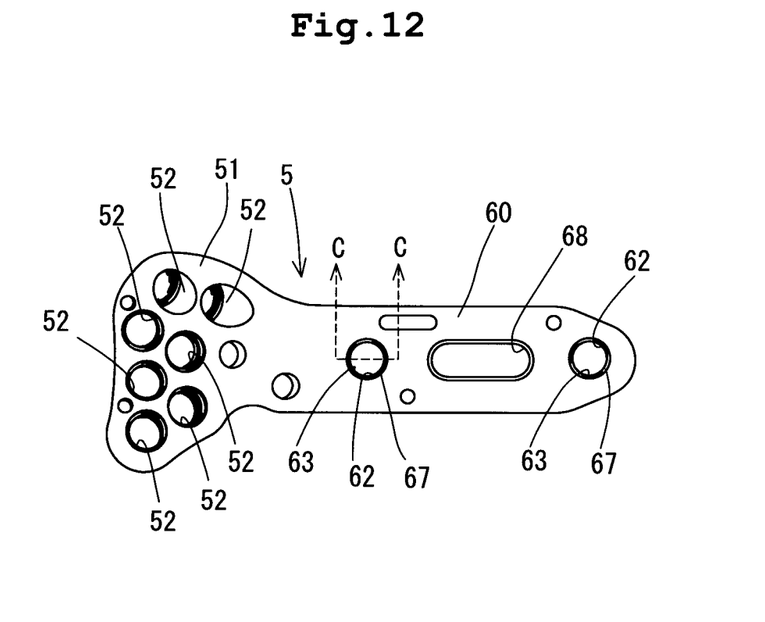
FIG. 12 is a plan view of a bone plate of the present invention for use in the bone treating device shown in FIG. 1.

The bone plate 5 of the present invention is described below. As shown in FIG. 12, the bone plate 5 is formed in the shape of a T-shaped thin plate in a planar view and has a head part 51 and a body 60. A large number of screw holes 52 is formed in penetration through the head part 51. Seven screw holes 52 are formed in penetration therethrough in this embodiment. The screw holes 52 are so formed that the axes thereof tilt at different angles. That is, there is a difference in removal direction of a plurality of screws (not shown in the drawings) fixed to the screw holes 52 respectively by threaded engagement therebetween with the shaft parts of the screws being fixed into the bone. Thus, even in a case where a male screw part is not formed in the shaft part of each screw, it is possible to prevent a plurality of the screws fixed into the bone from being removed therefrom owing to the cooperation of the shaft parts of the screws.

Along a longitudinal direction of the body plate 60, there is formed a plurality of the openings 62 (for example, two openings) for fixing the bone screw 2 to the plate body 60 formed continuously with the head part 51 at a right angle to a longitudinal direction of the head part 51. A fixing hole 68 having a rounded rectangular shape in a planar view is formed between the two openings 62. In an ordinary procedure, the bone plate is initially fixed to the bone by using the fixing hole 68 and a bone screw (not having a male screw part at its head part). The fixing hole 68 does not have a female screw part formed on its inner surface.

Figure 13:
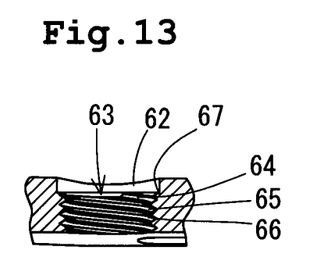
FIG. 13 is a sectional view of the bone screw shown in FIG. 12 taken along a line C-C.

As shown in FIG. 13, the female screw part 63 consisting of a triple threaded screw is formed on the inner surface of each of the two openings 62. The thread grooves of the female screw part 63 are formed in parallel with one another along the axis of the opening 62. Unlike the male screw part 34 formed on the head part 30 of the bone screw 2, first, second, and third thread grooves 64, 65, and 66 of the female screw part 63 have a start edge at almost the same position in the axial direction of the female screw part 63 and a terminal edge at almost the same position in the axial direction thereof. In other words, the female screw part 63 has three thread grooves in its entirety. In the vicinity of an upper edge of the opening 62, there is formed an accommodating concave portion 67 with which a lower surface of the flange portion 40 of the bone screw 2 can be brought into contact and which is capable of accommodating the flange portion 40 entirely or partly.

As materials for forming the bone screw 2 and the bone plate 5, it is preferable to use titanium alloys (for example, Ti-6Al-4V of JIST7401-2, ASTM F-136 Ti-6Al-4V ELI), pure titanium (for example, JIST7401-1), and stainless steel (for example, SUS304 and SUS316 of JISG4303).

The method for using the bone treating device 1 is described below.

After the bone plate 5 is placed at a portion of bone to be treated, the bone screw (not having a male screw part at its head part) is screwed into an arbitrary position of the elongated fixing hole 68. Thereafter a bone screw is appropriately selected from among the bone screw of the present invention, an ordinary bone screw not having the threaded engagement start guiding portion, and a bone screw of a pin type having a threadedly engaging portion which engages the screw hole 52 of the head part 51 but not having a screw part on the outer surface of the shaft part thereof. After selected bone screws are inserted into the bone from the screw holes 52 of the head part 51 respectively, the bone screws are fixed to the screw holes 52 respectively. Thereafter as shown in FIG. 1, the bone screw 2 of the present invention are screwed into the openings 62 of the plate body 60 and into the bone. As described above, the bone screw 2 has the self-tapping portion 22 at its distal end side. The self-tapping portion 22 is screwed into the bone with the self-tapping portion 22 cutting a portion of the bone disposed immediately below each opening 62. The self-tapping portion 22 penetrates the bone while the self-tapping portion 22 is cutting the portion of the bone to form a female screw part to be threadedly engaged by the screw portion 26 on the inner circumferential surface of a formed hole of the bone. The bone screw 2 is further screwed into the bone in the order of the first bone screw portion 27, the back tapered portion 28, and the second bone screw portion 29. The screw portion 26 has the second bone screw portion 29 whose outer diameter is formed slightly smaller than that of the first bone screw portion 27 and the back tapered portion 28 whose outer diameter becomes gradually smaller from the first bone screw portion 27 to the second bone screw portion 29. Thus, in an operation of screwing the portions of the screw portion 26 proximal from the first bone screw portion 27 into the bone, it is possible to slightly weaken the resistance of the inner circumferential surface of the formed hole of the bone to the portions of the screw portion 26 proximal from the first bone screw portion 27 and thus smoothly screw the screw portion 26 into the hole of the bone.

When almost all of the screw portion 26 is screwed into the bone, the male screw part 34, consisting of the triple threaded screw, which is formed in the head part 30 starts to threadedly engage the female screw part 63, consisting of the triple threaded screw, which is formed on the inner surface of the opening 62 of the plate body 60. At this time, as described above, the threaded engagement start guiding portion 36, consisting of the first screw thread 35, which is extended to the threaded engagement start side starts to threadedly engage the female screw part 63 of the bone plate 5 before the second and third screw threads 38 and 39 start to threadedly engage the female screw part 63. It is unnecessary for a plurality of the screw threads 35, 38, and 39 to engage the female screw part 63 all together, which does not necessitate the axis of the head part 30 and that of the female screw part 63 to align with each other in an early stage of the threaded engagement between the threaded engagement start guiding portion 36 and the male screw part 63. Thus, the head part 30 of the screw bone 2 is allowed to have a degree of freedom in its angle and position. With the progress of the engagement between the first screw thread 35 and the female screw part 63 to a certain extent, the angle and position of the head part 30 are gradually corrected and consequently the axis of the head part 30 and that of the female screw part 63 become aligned with each other. After the axis of the head part 30 and that of the female screw part 63 become aligned with each other, the second and third screw threads 38 and 39 start to threadedly engage the female screw part 63. Thus, it is possible to start the threaded engagement between the second and third screw threads 38 and 39 and the female screw part 63 at a right angle and position.

The bone screw 2 is further screwed into the bone to threadedly engage all of the screw threads, namely, the first, second, and third screw threads 35, 38, and 39 of the male screw part 34, consisting of the triple threaded screw, which are formed on the outer surface of the head part 30 of the bone screw 2 with all of the thread grooves, namely, the first, second, and third thread grooves 64, 65, and 66 of the female screw part 63, consisting of the triple threaded screw, which are formed on the inner surface of the opening 62 of the plate body 60 until the flange portion 40 of the bone screw 2 is brought into contact with the accommodating concave portion 67 of the opening 62 of the plate body 60 and accommodated therein. In this manner, the bone screw 2 is fixedly mounted on the bone plate 5.

Another embodiment of the present invention is described below with reference to FIGS. 14 and 15.

In the above-described bone treating device 1, the threaded engagement start guiding portion 36 is formed of the first screw thread 35 of the male screw part 34, of the bone screw 2, consisting of the triple threaded screw. In the bone treating device of this embodiment, a threaded engagement start guiding portion 77 is formed in a female screw part 63a of the bone plate 5, whereas the male screw part 34 of the head part 30 of the bone screw 2 consists entirely of the triple threaded screw and does not have the threaded engagement start guiding portion. In other words, each of the screw threads of the triple threaded screw is formed from the same position of the head part 30 in the axial direction thereof.

Figure 14:
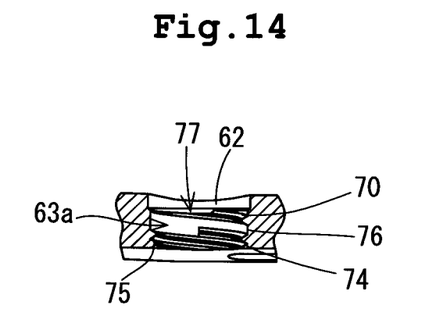
FIG. 14 is an enlarged sectional view of a bone plate of another embodiment of the present invention.

As shown in FIG. 14, the triple threaded screw of the female screw part 63a consists of first, second, and third thread grooves 70, 74, and 75. Of these three thread grooves, only the first thread groove 70 is extended to a threaded engagement start side, namely, to an upper side of the opening 62 of the female screw part 63a. A portion of the first thread groove 70 extended to the threaded engagement start side is formed as the threaded engagement start guiding portion 77. A portion of the female screw part 63a in the vicinity of the threaded engagement start guiding portion 77 is formed as a large diameter portion 76 by extending only one of a plurality of the thread grooves of the female screw part 63a to the threaded engagement start side. In other words, the threaded engagement start guiding portion 77 does not have a ridge other than two ridges which form one thread groove therebetween. Thus, the inner surface of the threaded engagement start guiding portion 77 forms a large diameter portion.

The first thread groove 70 forming the threaded engagement start guiding portion 77 is extended in a predetermined length about the axis of the female screw part 63a from an end of the threaded engagement start side of the second thread groove 74 and that of the third thread groove 75 in the axial direction of the female screw part 63a. The first screw thread 70 forming the threaded engagement start guiding portion 77 is extended at favorably not less than 180 degrees and more favorably not less than 270 degrees about the axis of the opening 62 from an end of the threaded engagement start side of the second thread groove 74 and that of the third thread groove 75. In this embodiment, the first screw thread 70 is extended at about 360 degrees about the axis of the opening 62 from an end of the threaded engagement start side of the second thread groove 74 and that of the third thread groove 75.

As in the case of the above-described embodiment, the female screw part 63a of the bone plate 5 is provided with the threaded engagement start guiding portion 77 in this embodiment. Thereby, the threaded engagement between the screw threads of the male screw part 34 of the head part 30 of the bone screw and the thread grooves of the female screw part 63a of the bone plate 5 starts when the screw thread of the male screw part 34 engage only the first thread groove 70. Therefore, it is unnecessary for the male screw part 34 of the bone screw to engage a plurality of the thread grooves 70, 74, and 75 all together, which does not necessitate the axis of the head part 30 of the bone screw and that of the female screw part 63a of the bone plate 5 to align with each other. Thus, the head part 30 of the bone screw is allowed to have a degree of freedom in its angle and position. With the progress of the threaded engagement between the screw threads of the male screw part 34 and the first thread groove 70 to a certain extent, the angle and position of the head part 30 of the bone screw are gradually corrected. As a result, the axis of the head part 30 of the bone screw and that of the female screw part 63a of the bone plate 5 become aligned with each other. By aligning the axis of the male screw of the head part 30 and that of the female screw part 63a of the bone plate 5 with each other, it becomes easy for the male screw of the head part 30 to engage the second and third thread grooves 74 and 75 which are not extended to the threaded engagement start side unlike the first thread groove 70 after the male screw of the bone screw engages the first thread groove 70. In the above-described embodiments, to form the threaded engagement start guiding portion on the bone screw and the bone plate 5, a semi-product as shown in FIG. 14 is produced by using a conventional screw producing method such as rolling to be performed by using a tap, a dice, and the like. Thereafter other than a screw thread and a thread groove of a part of a multiple threaded screw, remaining parts of the multiple threaded screw are cut off at the threaded engagement start side thereof.

Figure 15:
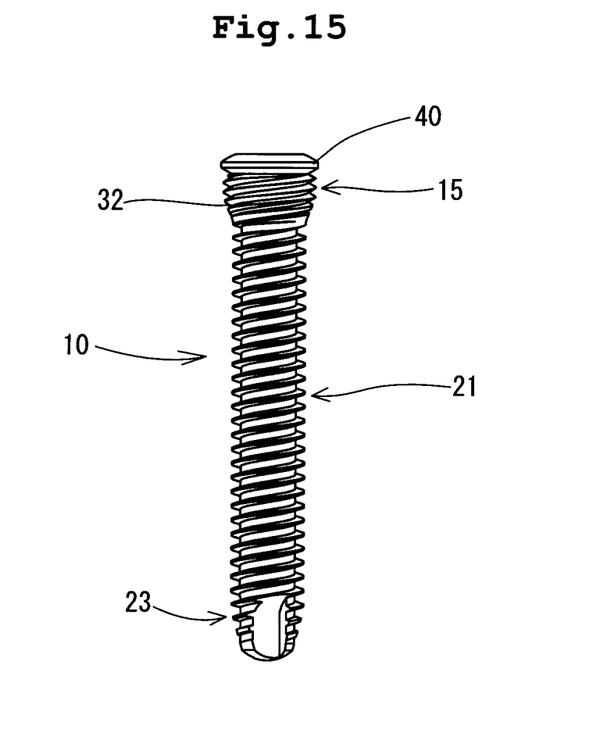
FIG. 15 is a right side view, of the bone screw shown in FIG. 1, which shows a state in which a part of a screw thread of a head part of the bone screw.

In the bone treating device of this embodiment, a bone screw 10 as shown in FIG. 15 is used. The bone screw 10 has the shaft part 21 and the head part 30. The shaft part 21 has the self-tapping portion 22 disposed at the distal end side thereof and the screw portion 26, to be inserted into bone, disposed at the side proximal from the self-tapping portion 22. The head part 30 of the bone screw 10 has the tapered portion 32 and the flange portion 40. The tapered portion 32 has the male screw part for fixing the bone screw 10 to the bone plate 5. The male screw part has a plurality of screw threads (specifically, three screw threads) in its entirety to form a threadedly engaging portion 15. The bone treating device of this embodiment does not have the threaded engagement start guiding portion unlike the above-described bone screw 2.

The embodiments of the bone treating device, bone screw, and bone plate of the present invention are not limited to the above-described ones, but can be appropriately altered within the range of the gist of the present invention. It is possible to use any bone treating device, bone screw, and bone plate, provided that the bone screw or the bone plate has the threaded engagement start guiding portion formed by extending screw threads or thread grooves whose number is fewer by at least one than the number of screw threads or thread grooves formed in the male screw part or the female screw part to the threaded engagement start side.

Although the triple threaded screw has been exemplified as the multiple threaded screw formed on the above-described bone screw or bone plate, it is possible to form a multiple threaded screw other than the triple threaded screw on the bone screw or the bone plate. For example, in a case where the number of screw threads and that of thread grooves formed on the male screw part and the female screw part are two, only one screw thread or only one thread groove is extended to the threaded engagement start side to form the threaded engagement start guiding portion. In a case where the number of screw threads and that of thread grooves formed on the male screw part and the female screw part are not less than four, not more than three screw threads or not more than three thread grooves are extended to the threaded engagement start side to form the threaded engagement start guiding portion. In this case, it is favorable to extend not more than two screw threads or not more than two thread grooves and more favorable to extend only one screw thread or only one thread groove to the threaded engagement start side to form the threaded engagement start guiding portion.

The construction of the bone treating device of the present invention is as described below.

(1) A bone treating device comprising a bone plate and a bone screw, wherein said bone plate has an opening which penetrates therethrough and has a female screw part having a plurality of thread grooves formed on an inner surface of said opening; said bone screw has a shaft part capable of penetrating said opening of said bone plate and a head part provided at a proximal end of said shaft part, said head part of said bone screw has a male screw part having a plurality of screw threads threadedly engageable with said thread grooves of said female screw part of said bone plate; and said bone screw or said bone plate has a threaded engagement start guiding portion formed by extending screw threads or thread grooves whose number is fewer by at least one than a number of screw threads or thread grooves formed in said male screw part or in said female screw part to a threaded engagement start side.

Therefore, the threaded engagement start guiding portion of the male screw part starts to threadedly engage the female screw part before other screw threads of the male screw part start to engage the female screw part. It is unnecessary for a plurality of the screw threads of the male screw part to engage the female screw part all together, which does not necessitate the axis of the head part of the bone screw and that of the female screw part of the bone plate to align with each other in an early stage of the threaded engagement between the threaded engagement start guiding portion of the male screw part and the female screw part. Thus, the head part of the bone screw is allowed to have a degree of freedom in its angle and position. With the progress of the engagement between the threaded engagement start guiding portion of the male screw part and female screw part to a certain extent after the threaded engagement start guiding portion of the male screw part threadedly engages the female screw part, the angle and position of the head part are gradually corrected and consequently the axis of the head part of the bone screw and that of the female screw part of the bone plate become aligned with each other. After the axis of the head part and that of the female screw part of the bone plate become aligned with each other, other screw threads of the male screw part start to threadedly engage the thread grooves of the female screw part. Thus, even though the bone plate and the bone screw have the multiple threaded screw, it is possible to easily threadedly engage the male screw part of the bone screw with the female screw part of the bone plate at a right angle and position.

The above-described embodiments may be carried out as follows:

(2) A bone treating device according to the above (1), wherein said threaded engagement start guiding portion is formed by extending only one of said screw threads or only one of said thread grooves formed in said male screw part or in said female screw part to said threaded engagement start side.

(3) A bone treating device according to the above (1), wherein said female screw part of said bone plate has not less than three thread grooves on said inner surface thereof; said male screw part of said bone screw has not less than three screw threads threadedly engageable with said thread grooves of said female screw part; and said threaded engagement start guiding portion is formed by extending one or two of said screw threads or one or two of said thread grooves formed in said male screw part or in said female screw part to said threaded engagement start side.

(4) A bone treating device according to the above (1), wherein said female screw part of said bone plate has two thread grooves on said inner surface thereof; said male screw part of said bone screw has two screw threads threadedly engageable with said thread grooves of said female screw part; and said threaded engagement start guiding portion is formed by extending only one of said screw threads or only one of said thread grooves formed in said male screw part or in said female screw part to said threaded engagement start side.

The construction of the bone screw of the present invention is as described below.

(5) A bone screw which can be fixed to a bone plate having an opening which has a female screw part having a plurality of thread grooves formed on an inner surface of said opening, said bone screw having a shaft part capable of penetrating said opening of said bone plate and a head part provided at a proximal end of said shaft part, wherein said head part has a male screw part having a plurality of screw threads threadedly engageable with said thread grooves of said bone plate; said bone screw has a threaded engagement start guiding portion formed by extending screw threads whose number is fewer by at least one than a number of said screw threads formed in said male screw part to a threaded engagement start side.

The above-described embodiments may be carried out as follows:

(6) A bone screw according to the above (5), wherein said threaded engagement start guiding portion is formed by extending only one of said screw threads formed in said male screw part to said threaded engagement start side.

(7) A bone screw according to the above (5), wherein said female screw part of said bone plate has not less than three thread grooves; said male screw part of said bone screw has not less than three screw threads threadedly engageable with said thread grooves of said female screw part; and said threaded engagement start guiding portion is formed by extending one or two of said screw threads formed in said male screw part to said threaded engagement start side.

(8) A bone screw according to the above (5), wherein said shaft part has a male screw to be inserted into bone, and said male screw has a lead almost equal to leads of a plurality of said screw threads.

(9) A bone screw according to the above (5), wherein said shaft part has a self-tapping portion provided at a distal end side of said shaft part.

The construction of the bone screw of the present invention is as described below.

(10) A bone plate having an opening for fixing a bone screw thereto,
wherein said opening has a female screw part having a plurality of thread grooves formed on an inner surface thereof and a threaded engagement start guiding portion formed by extending thread grooves whose number is fewer by at least one than a number of said thread grooves formed in said female screw part to a threaded engagement start side.

The above-described embodiments may be carried out as follows:

(11) A bone plate according to the above (10), wherein said threaded engagement start guiding portion is formed by extending only one of said thread grooves formed in said female screw part to said threaded engagement start side.

(12) A bone plate according to the above (10), wherein said female screw part has not less than three thread grooves; and said threaded engagement start guiding portion is formed by extending one or two of said thread grooves formed in said female screw part to said threaded engagement start side of said opening.

(13) A bone plate according to the above (10), which has a plurality of said openings.

The invention claimed is:

1. A bone treating device, comprising:
   a bone plate; and
   a bone screw, wherein
   said bone plate has an opening which penetrates therethrough and has a female screw part having a plurality of thread grooves formed on an inner surface of said opening;
   said bone screw has a shaft part capable of penetrating said opening of said bone plate and a head part provided at a proximal end of said shaft part,
   said head part of said bone screw has a male screw part having a plurality of screw threads threadedly engageable with said thread grooves of said female screw part of said bone plate;
   said bone screw or said bone plate has a threaded engagement start guiding portion formed by extending screw threads or thread grooves whose number is fewer by at least one than a number of screw threads or thread grooves formed in said male screw part or in said female screw part to a threaded engagement start side, and said threaded engagement start guiding portion has a smooth surface portion not having said screw threads or said thread grooves and which is formed by a reduction of the number of said screw threads or said thread grooves.

2. The bone treating device according to claim 1, wherein said threaded engagement start guiding portion is formed by extending only one of said screw threads or only one of said thread grooves formed in said male screw part or in said female screw part to said threaded engagement start side.

3. The bone treating device according to claim 1, wherein said female screw part of said bone plate has not less than three thread grooves on said inner surface thereof; said male screw part of said bone screw has not less than three screw threads threadedly engageable with said thread grooves of said female screw part; and said threaded engagement start guiding portion is formed by extending one or two of said screw threads or one or two of said thread grooves formed in said male screw part or in said female screw part to said threaded engagement start side.

4. The bone treating device according to claim 1, wherein said female screw part of said bone plate has two thread grooves on said inner surface thereof; said male screw part of said bone screw has two screw threads threadedly engageable with said thread grooves of said female screw part; and said threaded engagement start guiding portion is formed by extending only one of said screw threads or only one of said thread grooves formed in said male screw part or in said female screw part to said threaded engagement start side.

5. A bone screw which can be fixed to a bone plate having an opening which has a female screw part having a plurality of thread grooves formed on an inner surface of said opening, said bone screw comprising:
a shaft part capable of penetrating said opening of said bone plate; and
a head part provided at a proximal end of said shaft part, wherein
said head part has a male screw part having a plurality of screw threads threadedly engageable with said thread grooves of said bone plate;
said bone screw has a threaded engagement start guiding portion formed by extending screw threads whose number is fewer by at least one than a number of said screw threads formed in said male screw part to a threaded engagement start side, and
said threaded engagement start guiding portion has a smooth surface portion not having said screw threads and which is formed by a reduction of the number of said screw threads.

6. The bone screw according to claim 5, wherein said threaded engagement start guiding portion is formed by extending only one of said screw threads formed in said male screw part to said threaded engagement start side.

7. The bone screw according to claim 5, wherein said female screw part of said bone plate has not less than three thread grooves; said male screw part of said bone screw has not less than three screw threads threadedly engageable with said thread grooves of said female screw part; and said threaded engagement start guiding portion is formed by extending one or two of said screw threads formed in said male screw part to said threaded engagement start side.

8. The bone screw according to claim 5, wherein said shaft part has a male screw to be inserted into bone, and said male screw has a lead substantially equal to leads of a plurality of said screw threads.

9. The bone screw according to claim 5, wherein said shaft part has a self-tapping portion provided at a distal end side of said shaft part.

10. The bone screw according to claim 5, wherein:
said male screw part of said bone screw has three screw threads having substantially equal lead,
said threaded engagement start guiding portion is formed by extending one of said screw threads formed in said male screw part to said threaded engagement start side, and
the other two of said screw threads are not extended to said threaded engagement start guiding portion.

11. The bone screw according to claim 5, wherein said smooth surface portion has a same height as a bottom of said screw threads.

12. A bone plate, comprising:
a plate portion; and
an opening in the plate portion for fixing a bone screw thereto,
wherein said opening has a female screw part having a plurality of thread grooves formed on an inner surface thereof, a threaded engagement start guiding portion formed by extending thread grooves whose number is fewer by at least one than a number of said thread grooves formed in said female screw part to a threaded engagement start side, and said threaded engagement start guiding portion has a smooth surface portion not having said thread grooves and which is formed by a reduction of the number of said thread grooves.

13. The bone plate according to claim 12, wherein said threaded engagement start guiding portion is formed by extending only one of said thread grooves formed in said female screw part to said threaded engagement start side.

14. The bone plate according to claim 12, wherein said female screw part has not less than three thread grooves; and said threaded engagement start guiding portion is formed by extending one or two of said thread grooves formed in said female screw part to said threaded engagement start side of said opening.

15. The bone plate according to claim 12, which has a plurality of said openings.

16. The bone plate according to claim 12, wherein:
said female screw part of said bone plate has three thread grooves,
said threaded engagement start guiding portion is formed by extending one of said thread grooves formed in said female screw part to said threaded engagement start side of opening, and
the other two of said thread grooves are not extended to said threaded engagement start guiding portion.

17. The bone plate according to claim 12, wherein said threaded engagement start guiding portion does not have a ridge other than two ridges which form one thread groove therebetween, and said smooth surface portion not having said thread grooves forms a large diameter portion.

* * * * *